(12) United States Patent
Nunome et al.

(10) Patent No.: US 6,843,772 B2
(45) Date of Patent: Jan. 18, 2005

(54) INFERIOR-AND-SUPERIOR-LIMB BLOOD-PRESSURE-INDEX MEASURING APPARATUS

(75) Inventors: Tomohiro Nunome, Komaki (JP); Kiyoyuki Narimatsu, Komaki (JP); Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 9 days.

(21) Appl. No.: 10/300,824

(22) Filed: Nov. 21, 2002

(65) Prior Publication Data

US 2003/0109789 A1 Jun. 12, 2003

(30) Foreign Application Priority Data

Dec. 6, 2001 (JP) .................................... 2001-372500
May 10, 2002 (JP) .................................... 2002-134974

(51) Int. Cl.[7] ............................................. A61B 5/02
(52) U.S. Cl. ................................... 600/481; 600/485
(58) Field of Search ............................... 600/481–507, 600/465

(56) References Cited

U.S. PATENT DOCUMENTS

| | | | | |
|---|---|---|---|---|
| 5,050,613 A | * | 9/1991 | Newman et al. ............. | 600/483 |
| 5,715,826 A | * | 2/1998 | Horrocks et al. ........... | 600/485 |
| 6,355,000 B1 | | 3/2002 | Ogura | |
| 6,379,309 B1 | * | 4/2002 | Ogura et al. ................ | 600/490 |
| 6,524,257 B2 | * | 2/2003 | Ogura ........................ | 600/490 |
| 6,676,608 B1 | * | 1/2004 | Keren ........................ | 600/481 |

FOREIGN PATENT DOCUMENTS

| | | |
|---|---|---|
| DE | 199 60 452 A1 | 8/2001 |
| EP | 1 050 266 A1 | 11/2000 |
| EP | 1 050 267 A1 | 11/2000 |
| EP | 1 053 714 A2 | 11/2000 |
| EP | 1 240 866 A1 | 9/2002 |
| JP | B2 3140007 | 12/2000 |

OTHER PUBLICATIONS

Simon et al., "Feasibility and Reliability of Ankle/Arm Blood Pressure Index in Preventive Medicine", Angiology, Jun. 2000; 51,6, pp. 463–471.*

* cited by examiner

Primary Examiner—Max F. Hindenburg
Assistant Examiner—Patricia Mallari
(74) Attorney, Agent, or Firm—Oliff & Berridge, PLC

(57) ABSTRACT

An apparatus for measuring an inferior-and-superior-limb blood-pressure index of a patient, including an inferior-limb blood-pressure measuring device, a superior-limb blood-pressure measuring device, an index determining device for determining the inferior-and-superior-limb blood-pressure index, based on a blood pressure of an inferior limb measured by the inferior-limb blood-pressure measuring device and a blood pressure of a superior limb measured by the superior-limb blood-pressure measuring device, an inferior-limb-pulse-wave-propagation-velocity-related-information obtaining device which obtains inferior-limb-pulse-wave-propagation-velocity-related information, an upper-half-body-pulse-wave-propagation-velocity-related-information obtaining device which obtains upper-half-body-pulse-wave-propagation-velocity-related information, and an evaluation-information obtaining device for obtaining, based on the inferior-limb-pulse-wave-propagation-velocity-related information and the upper-half-body-pulse-wave-propagation-velocity-related information, evaluation information that is related to evaluation of reliability of the inferior-and superior-limb blood-pressure index.

7 Claims, 7 Drawing Sheets

INFERIOR-AND-SUPERIOR-LIMB BLOOD-PRESSURE-INDEX MEASURING APPARATUS

BACKGROUND OF THE INVENTION

1. Field of the Invention

The present invention relates to an inferior-and-superior-limb blood-pressure-index measuring apparatus which measures an inferior-and-superior-limb blood-pressure index of a living subject.

2. Related Art Statement

An inferior-and-superior-limb blood-pressure index is generally known as a ratio of a blood pressure of a superior limb of a living subject to a blood pressure of an inferior limb of the subject, or a ratio of the blood pressure of the inferior limb to that of the superior limb. Respective systolic blood pressures of the inferior and superior limbs are generally used as the respective blood pressures of those limbs. In addition, generally, an ankle is selected as the inferior limb and an upper arm is selected as the superior limb, so that an ankle-and-upper-arm blood-pressure index is determined as the inferior-and-superior-limb blood-pressure index. The inferior-and-superior-limb blood-pressure index represented by the ankle-and-upper-arm blood-pressure index is useful in making a diagnosis about stenosis or obliteration caused by atheromatous arteriosclerosis (atherosclerosis). If a living subject has stenosis in a portion of an artery, subject's blood pressure lowers on a downstream side of the stenotic portion, which leads to showing an abnormal inferior-and-superior-limb blood-pressure index. Thus, stenonis of artery can be diagnosed based on inferior-and-superior-limb blood-pressure index. In many cases, stenosis of artery occurs to inferior limbs of a human person.

Since inferior-and-superior-limb blood-pressure index is a simple ratio, i.e., a ratio of one of inferior-limb blood pressure and superior-limb blood pressure to the other, reliable measurement of inferior-and-superior-limb blood-pressure index requires that inferior-limb blood pressure and superior-limb blood pressure be measured with accuracy. There is known a different sort of arteriosclerosis than atherosclerosis, that is, "calcification". If calcification of an artery advances, blood pressure in the artery increases because of hardening of the wall of artery. If the calcification of the artery further advances, the artery cannot be completely closed and the blood pressure further increases. Thus, even if an artery of an inferior limb has stenosis, a normal inferior-and-superior-limb blood-pressure index value may be obtained if the artery suffers advanced calcification.

Hence, there has been proposed an inferior-and-superior-limb blood-pressure-index measuring apparatus which simultaneously displays an inferior-and-superior-limb blood-pressure index, and pulse-wave-propagation-velocity-related information, such as a pulse-wave propagation velocity, or a corrected pulse-wave propagation velocity which is obtained by correcting a pulse-wave propagation velocity so as to correspond to a pre-selected blood pressure, so that when the inferior-and-superior-limb blood-pressure index being displayed is normal, it can be judged by a medical person whether the normal index means that the inferior limb's artery does not have stenosis or that the artery has not only stenosis but also advanced calcification. This apparatus is disclosed in Japanese Patent No. 3,140,007 or its corresponding U.S. Pat. No. 6,355,000. Pulse-wave-propagation-velocity-related information, such as a pulse-wave propagation velocity, can be used to evaluate a degree of calcification of artery. Since the apparatus simultaneously displays an inferior-and-superior-limb blood-pressure index and pulse-wave-propagation-velocity-related information, an accurate judgment can be made about whether a patient has arteriostenosis. In the following description of the present application, pulse-wave propagation velocity and pulse-wave propagation time, and corrected pulse-wave propagation velocity and corrected pulse-wave propagation time which are obtained by correcting pulse-wave propagation velocity and pulse-wave propagation time, respectively, so as to correspond to a pre-selected blood pressure, are all defined as pulse-wave-propagation-velocity-related information.

A living subject who has normal blood vessels, such as a young person, has substantially no difference between his or her inferior-limb and superior-limb blood pressure values, and accordingly an inferior-and-superior-limb blood-pressure index value of the subject should be around one. However, in some cases, a measurement error or malfunction may abnormally lower the inferior-limb blood pressure, thereby showing an abnormal inferior-and-superior-limb blood-pressure index. However, the above-indicated conventional inferior-and-superior-limb blood-pressure-index measuring apparatus cannot judge, when the blood-pressure index is abnormal, whether the abnormal index has resulted from the stenosis of inferior limb or the abnormality of blood-pressure measurement. Pulse-wave-propagation-velocity-related information changes in relation with calcification of artery and, at the same time, changes in relation with stenosis of artery. However, calcification of artery and stenosis of artery influence pulse-wave-propagation-velocity-related information in "opposite" directions. More specifically described using pulse-wave propagation velocity as a sort of pulse-wave-propagation-velocity-related information, as the calcification of artery advances, the propagation velocity increases but, as the stenosis of artery advances, the propagation velocity decreases. Therefore, if an artery simultaneously suffers advanced calcification and stenosis, then the pulse-wave-propagation-velocity-related information obtained from the artery may be normal, or around a normal range. It is natural that pulse-wave-propagation-velocity-related information obtained from a living subject whose blood vessels are normal should be normal. Thus, the above-indicated conventional inferior-and superior-limb blood-pressure-index measuring apparatus cannot judge, when a measured inferior-and-superior-limb blood-pressure index is abnormal, whether the abnormal index has resulted from stenosis of inferior limb or abnormality of blood-pressure measurement.

In addition, normal range of pulse-wave-propagation-velocity-related information largely changes among individual subjects, and more or less changes on each subject depending on his or her physical condition. However, the inferior-and-superior-limb blood-pressure-index measuring apparatus disclosed by the above-indicated Japanese Patent No. 3,140,007 obtains only a single sort of pulse-wave-propagation-velocity-related information so as to recognize lowering of reliability of inferior-and-superior-limb blood-pressure index that is caused by calcification of artery. In this case, a medical person must evaluate the blood-pressure index while taking into account the individual differences of patients and/or the physical condition of each patient, and accordingly cannot make a sufficiently accurate evaluation.

SUMMARY OF THE INVENTION

It is therefore an object of the present invention to provide an inferior-and-superior-limb blood-pressure-index measuring apparatus which can accurately evaluate reliability of an inferior-and-superior-limb blood-pressure index of a living subject.

The above object has been achieved by the present invention. According to a first aspect of the present invention, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; an inferior-limb-pulse-wave-propagation-velocity-relatedinformation obtaining device which obtains inferior-limb-pulse-wave-propagation-velocity-related information that is related to a velocity at which an inferior-limb pulse wave propagates in a first portion of the subject that includes the inferior limb; an upper-half-body-pulse-wave-propagation-velocity-relatedinformation obtaining device which obtains upper-half-body-pulse-wave-propagation-velocity-related information that is related to a velocity at which an upper-half-body pulse wave propagates in a second portion of an upper half body of the subject; and an evaluation-information obtaining means for obtaining, based on comparison of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device, evaluation information that is related to evaluation of reliability of the inferior-and-superior-limb blood-pressure index determined by the inferior-and-superior-limb-blood-pressure-index determining means.

According to this invention, the evaluation-information obtaining means obtains the evaluation information based on the comparison of the inferior-limb-pulse-wave-propagation-velocity-related information and the upper-half-body-pulse-wave-propagation-velocity-related information. Here, the inferior-limb-pulse-wave-propagation-velocity-related information is pulse-wave-propagation-velocity-related information obtained from the prescribed portion including the inferior limb, and accordingly indicates arteriosclerosis of the portion including the inferior limb; and the upper-half-body-pulse-wave-propagation-velocity-related information is pulse-wave-propagation-velocity-related information obtained from the prescribed portion of the upper half body, i.e., a portion not including any inferior limbs, and accordingly indicates arteriosclerosis of the portion not including any inferior limbs. Therefore, if the inferior limb has stenosis, the inferior-limb-pulse-wave-propagation-velocity-related information is influenced by the stenosis, but the upper-half-body-pulse-wave-propagation-velocity-related information is not influenced by it. Thus, based on the comparison of the inferior-limb-pulse-wave-propagation-velocity-related information and the upper-half-body-pulse-wave-propagation-velocity-related information, the present apparatus can obtain the evaluation information useful in evaluating the reliability of the superior-and-inferior-limb blood-pressure index. In addition, since the evaluation information are obtained based on the inferior-limb-pulse-wave-propagation-velocity-related information and the upper-half-body-pulse-wave-propagation-velocity-related information both of which are obtained from the same subject, the evaluation information is hardly influenced by individual differences of subjects and/or physical condition of each subject. Thus, the present apparatus can accurately evaluate the reliability of the superior-and-inferior-limb blood-pressure index.

According to a preferred feature of the first aspect of the invention, the inferior-limb blood-pressure measuring device includes the inferior-limb cuff adapted to be wound around an ankle of the subject and measures a blood pressure of the ankle, the superior-limb blood-pressure measuring device includes the superior-limb cuff adapted to be wound around an upper arm of the subject and measures a blood pressure of the upper arm, the inferior-limb-pulse-wave-propagation-velocity-relatedinformation obtaining device obtains the inferior-limb-pulse-wave-propagation-velocity-related information related to the velocity at which the inferior-limb pulse wave propagates in the first portion of the subject that includes the ankle and the upper arm, and the upper-half-body-pulse-wave-propagation-velocityrelated-information obtaining device obtains the upper-half-body-pulse-wave-propagation-velocity-related information related to the velocity at which the upper-half-body pulse wave propagates in the second portion of the upper half body of the subject that includes a portion between the heart of the subject and the upper arm.

According to a second aspect of the present invention, inferior-limb-pulse-wave-propagation-velocity-related information and superior-limb-pulse-wave-propagation-velocity-related information are obtained from different portions of a living subject than those portions from which the two sorts of information are obtained according to the above-indicated first aspect. According to the second aspect, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; an inferior-limb-pulse-wave-propagation-velocity-related-information obtaining device which obtains inferior-limb-pulse-wave-propagation-velocity-related information that is related to a velocity at which an inferior-limb pulse wave propagates in a first portion of the inferior limb of the subject; an upper-halfbody-pulse-wave-propagation-velocity-related-information obtaining device which obtains upper-half-body-pulse-wave-propagation-velocity-related information that is related to a velocity at which an upper-half-body pulse wave propagates in a second portion of the subject that includes an upper half body of the subject; and an evaluation-information obtaining means for obtaining, based on comparison of the inferior-limb-pulse-wavepropagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device, evaluation information that is related to evaluation of reliability of the inferior-and-superior-limb blood-pressure index determined by the inferior-and superior-limb-blood-pressure-index determining means.

According to this invention, the evaluation information obtaining means obtains the evaluation information based on the comparison of the inferior-limb-pulse-wave-propagation-velocity-related information and the upper-half-body-pulse-wave-propagation-velocity-related information. Here, the inferior-limb-pulse-wave-propagation-velocity-related information is pulse-wave-propagation-velocity-related information obtained from the prescribed portion of the inferior limb, and accordingly indicates arteriosclerosis of the portion including at least a portion of the inferior limb but not including any portions of the upper half body; and the upper-half-body-pulse-wave-propagation-velocity-related information is pulse-wave-propagation-velocity-related information obtained from the prescribed portion including the upper half body, and accordingly indicates arteriosclerosis of the portion including the upper half body. Therefore, if the inferior limb has stenosis, the inferior-limb-pulse-wave-propagation-velocity-related information is largely influenced by the stenosis, but the upper-half-body-pulse-wave-propagation-velocity-related information is not, or little, influenced by it. Thus, based on the comparison of the inferior-limb-pulse-wave-propagation-velocity-related information and the upper-half-body-pulse-wave-propagation-velocity-related information, the present apparatus can obtain the evaluation information useful in evaluating the reliability of the superior-and-inferior-limb blood-pressure index. In addition, since the evaluation information are obtained based on the inferior-limb-pulse-wave-propagation-velocity-related information and the upper-half-body-pulse-wave-propagation-velocity-related information both of which are obtained from the same subject, the evaluation information is hardly influenced by individual differences of subjects and/or physical condition of each subject. Thus, the present apparatus can accurately evaluate the reliability of the superior-and-inferior-limb blood-pressure index.

According to a preferred feature of each of the first and second aspects of the invention, the evaluation-information obtaining means obtains, as the evaluation information, a ratio of one of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wavepropagation-velocity-related-information obtaining device to the other of the inferior-limb-pulse-wave-propagation-velocity-related information and the upper-half-body-pulse-wave-propagation-velocity-related information. In this case, the reliability of the inferior-and-superior-limb blood-pressure index can be easily evaluated.

According to another preferred feature of each of the first and second aspects of the invention, the evaluation-information obtaining means obtains, as the evaluation information, a difference of one of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device from the other of the inferior-limb-pulse-wave-propagation-velocity-related information and the upper-half-body-pulse-wave-propagation-velocity-related information.

According to another preferred feature of each of the first and second aspects of the invention, the evaluation-information obtaining means judges whether the ratio of the one of the inferior-limb-pulse-wave-propagation-velocity-related information and the upper-half-body-pulse-wave-propagation-velocity-related information to the other of the inferior-limb-pulse-wave-propagation-velocity-related information and the upper-half-body-pulse-wave-propagation-velocity-related information falls within a preset normal range, and thereby automatically judges whether the inferior-and-superior-limb blood-pressure index is reliable. In the latter case, the evaluation information may comprise the result of judgment.

According to another preferred feature of each of the first and second aspects of the invention, the evaluation-information obtaining means judges whether the difference of the one of the inferior-limb-pulse-wave-propagation-velocity-related information and the upper-half-body-pulse-wave-propagation-velocity-related information from the other of the inferior-limb-pulse-wave-propagation-velocity-related information and the upper-half-body-pulse-wave-propagation-velocity-related information falls within a preset normal range, and thereby automatically judges whether the inferior-and-superior-limb blood-pressure index is reliable.

According to a third aspect of the present invention, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; an inferior-limb-pulse-wave-propagation-velocity-related-information obtaining device which obtains inferior-limb-pulse-wave-propagation-velocity-related information that is related to a velocity at which an inferior-limb pulse wave propagates in a first portion of the subject that includes the inferior limb; an upper-half-body-pulse-wave-propagation-velocity-relatedinformation obtaining device which obtains upper-half-body-pulse-wave-propagation-velocity-related information that is related to a velocity at which an upper-half-body pulse wave propagates in a second portion of an upper half body of the subject; and a display device which displays a graphical representation of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wavepropagation-velocity-related-information obtaining device, in a two-dimensional coordinate system which is defined by a first axis indicative of inferior-limb-pulse-wave-propagation-velocity-related information and a second axis indicative of upper-half-body-pulse-wave-propagation-velocity-related information, and which includes indication of a normal range of upper-half-body-pulse-wave-propagation-velocity-related information relative to inferior-limb-pulse-wave-propagation-velocity-related information.

According to this invention, the display device displays the graphical representation of the inferior-limb-pulse-wave-propagation-velocity-related information and the upper-half-body-pulse-wave-propagation-velocity-related information, in a two-dimensional coordinate system including indication of a normal range of upper-half-body-pulse-wave-propagation-velocity-related information relative to inferior-limb-pulse-wave-propagation-velocity-related information. Thus, it can be easily judged whether the relationship between the inferior-limb-pulse-wave-propagation-velocity-related information and the upper-half-body-pulse-wave-propagation-velocity-related information is normal, and accordingly the reliability of the inferior-and-superior-limb blood-pressure index can be easily evaluated.

According to a fourth aspect of the present invention, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; an inferior-limb-pulse-wave-propagation-velocity-related-information obtaining device which obtains inferior-limb-pulse-wave-propagation-velocity-related information that is related to a velocity at which an inferior-limb pulse wave propagates in a first portion of the inferior limb of the subject; an upper-halfbody-pulse-wave-propagation-velocity-related-information obtaining device which obtains upper-half-body-pulse-wave-propagation-velocity-related information that is related to a velocity at which an upper-half-body pulse wave propagates in a second portion of the subject that includes an upper half body of the subject; and a display device which displays a graphical representation of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wavepropagation-velocity-related-information obtaining device, in a two-dimensional coordinate system which is defined by a first axis indicative of inferior-limb-pulse-wave-propagation-velocity-related information and a second axis indicative of upper-half-body-pulse-wave-propagation-velocity-related information, and which includes indication of a normal range of upper-half-body-pulse-wave-propagation-velocity-related information relative to inferior-limb-pulse-wave-propagation-velocity-related information.

According to this invention, the display device displays the graphical representation of the inferior-limb-pulse-wave-propagation-velocity-related information and the upper-half-body-pulse-wave-propagation-velocity-related information, in a two-dimensional coordinate system including indication of a normal range of upper-half-body-pulse-wave-propagation-velocity-related information relative to inferior-limb-pulse-wave-propagation-velocity-related information. Thus, it can be easily judged whether the relationship between the inferior-limb-pulse-wave-propagation-velocity-related information and the upper-half-body-pulse-wave-propagation-velocity-related information is normal, and accordingly the reliability of the inferior-and-superior-limb blood-pressure index can be easily evaluated.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
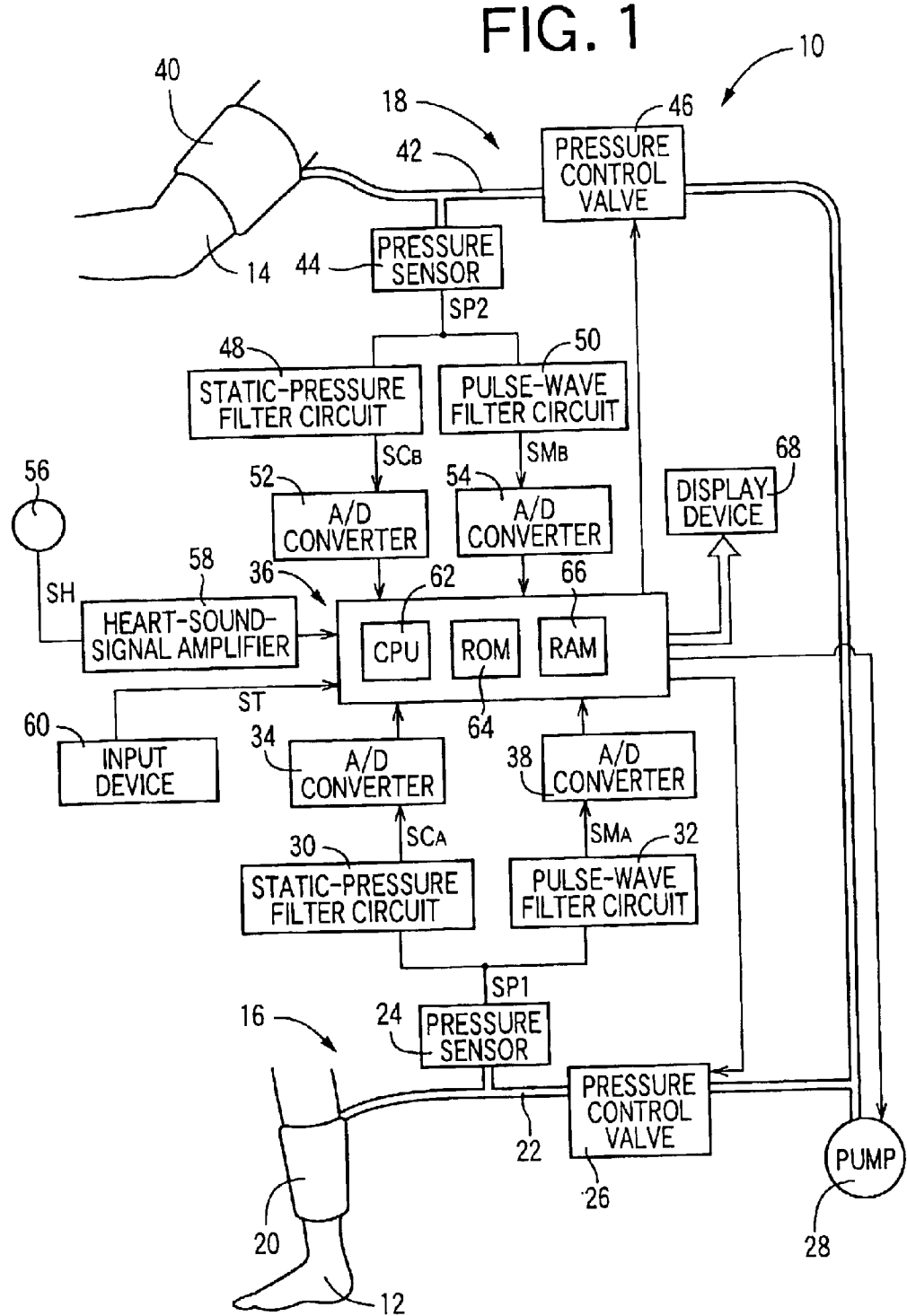
FIG. 1 is a diagrammatic view for explaining a construction of an ankle-and-upper-arm blood-pressure-index measuring apparatus to which the present invention is applied.

Hereinafter, there will be described a preferred embodiment of the present invention in detail by reference to the drawings. FIG. 1 is a diagrammatic view for explaining a construction of an ankle-and-upper-arm blood-pressure-index measuring apparatus 10 to which the present invention is applied. The ankle-and-upper-arm blood-pressure-index measuring apparatus 10, shown in FIG. 1, functions as an inferior-and-superior-limb blood-pressure-index measuring apparatus wherein an ankle 12 is selected as an inferior limb and an upper arm 14 is selected as a superior limb. The present apparatus 10 carries out measurements on a patient as a living subject who takes a face-up, a lateral, or a face-down position so that the upper arm and ankle of the patient are substantially level with each other.

In FIG. 1, the ankle-and-upper-arm blood-pressure (BP) index measuring apparatus 10 includes an ankle BP measuring device 16 which measures a BP value of the ankle 12 and which functions as an inferior-limb BP measuring device, and an upper-arm BP measuring device 18 which measures a BP value of the upper arm 14 and functions as a superior-limb BP measuring device.

The ankle BP measuring device 16 includes an ankle cuff 20 which includes a belt-like cloth bag and a rubber bag accommodated in the cloth bag and which is adapted to be wound around the ankle 12 of the patient; a piping 22; and a pressure sensor 24, a pressure control valve 26, and an air pump 28 which are connected to the ankle cuff 20 via the piping 22. The pressure control valve 26 adjusts a pressure of a pressurized air supplied from the air pump 28, and supplies the pressure-adjusted air to the ankle cuff 20, or discharges the pressurized air from the ankle cuff 22, so as to control an air pressure in the ankle cuff 20.

The pressure sensor 24 detects the air pressure in the ankle cuff 20, and supplies a pressure signal, SP1, representing the detected air pressure, to a static-pressure filter circuit 30 and a pulse-wave filter circuit 32. The static-pressure filter circuit 30 includes a low-pass filter which extracts, from the pressure signal SP1, an ankle-cuff-pressure signal, $SC_A$, representing a static component of the detected air pressure, i.e., a pressing pressure of the ankle cuff 20 (hereinafter, referred to as the ankle-cuff pressure, $PC_A$). The filter circuit 30 supplies the ankle-cuff-pressure signal $SC_A$ to an electronic control device 36 via an A/D (analog-to-digital) converter 34.

The pulse-wave filter circuit 32 includes a band-pass filter which extracts, from the pressure signal SP1, an ankle-pulse-wave signal, $SM_A$, representing an ankle pulse wave as an oscillatory component of the detected air pressure that has prescribed frequencies. The filter circuit 32 supplies the ankle-pulse-wave signal $SM_A$ to the control device 36 via an A/D converter 38. Since the ankle pulse wave indicates the oscillation of pressure of the ankle cuff 20, the filter circuit 32 functions as an ankle-pulse-wave detecting device.

The upper-arm BP measuring device 18 includes an upper-arm cuff 40 having a construction identical with that of the cuff of the ankle BP measuring device 16; and a piping 42, a pressure sensor 44, and a pressure control valve 46. The upper-arm cuff 40 is wound around the upper arm 14. The pressure control valve 46 is connected to the air pump 28. The pressure sensor 44 detects an air pressure in the upper-arm cuff 40, and supplies a pressure signal, SP2, representing the detected air pressure, to a static-pressure filter circuit 48 and a pulse-wave filter circuit 50 which have respective constructions identical with those of the counterparts of the ankle BP measuring device 16. The static-pressure filter circuit 48 extracts, from the pressure signal SP2, an upper-arm-cuff-pressure signal, $SC_B$, representing a static component of the detected air pressure, i.e., a pressing pressure of the upper-arm cuff 40 (hereinafter, referred to as the upper-arm-cuff pressure, $PC_B$). The filter circuit 48 supplies the upper-arm-cuff-pressure signal $SC_B$ to the control device 36 via an A/D converter 52. The pulse-wave filter circuit 50 extracts, from the pressure signal SP2, an upper-arm-pulse-wave signal, $SM_B$, representing an upper-arm pulse wave as an oscillatory component of the detected air pressure that has prescribed frequencies. The filter circuit 50 supplies the upper-arm-pulse-wave signal $SM_B$ to the control device 36 via an A/D converter 54. Since the upper-arm pulse wave indicates the oscillation of pressure of the upper-arm cuff 40, the filter circuit 50 functions as an upper-arm-pulse-wave detecting device.

A heart-sound microphone 56 is fixed, with an adhesive tape or the like, not shown, to a chest of the subject, not shown. The microphone 56 that is a heartbeat-synchronous-signal detecting device which detects a heart sound as a heartbeat-synchronous signal, incorporates a piezoelectric element, not shown, which converts heart sounds produced from the heart of the subject, into an electric signal, i.e., a heart-sound signal SH. A heart-sound-signal amplifier 58 includes four sorts of filters, not shown, which cooperate with one another to attenuate a low-pitch component having a great energy and thereby amplifies and filters a high-pitch component of the heart-sound signal SH supplied from the microphone 56. The heart-sound signal SH amplified and filtered by the amplifier 58 is supplied to the control device 36 via an A/D converter, not shown.

An input device 60 includes a plurality of keys, not shown, which are operated by an operator such as a doctor or a nurse to input a stature, T, of the patient. The input device 60 supplies a stature signal ST representing the inputted patient's stature T, to the control device 36.

The control device 36 is essentially provided by a microcomputer including a CPU (central processing unit) 62, a ROM (read only memory) 64, a RAM (random access memory) 66, and an I/O (input-and-output) port, not shown, and the CPU 62 processes signals according to the programs pre-stored in the ROM 64, while utilizing the data-storing function of the RAM 66. The control device 36 outputs, from the I/O port, drive signals to the air pump 28 and the two pressure control valves 26, 46 so as to control the respective operations thereof and thereby control the respective air pressures of the ankle cuff 26 and the upper-arm cuff 46. In addition, the CPU 62 processes signals supplied to the control device 36, so as to determine an ankle-and-upper-arm BP index (or an Ankle Arm Blood Pressure Index; hereinafter, referred to as an ABI value) and evaluation information, and control a display device 68 to display the thus determined ABI value and evaluation information.

Figure 2:
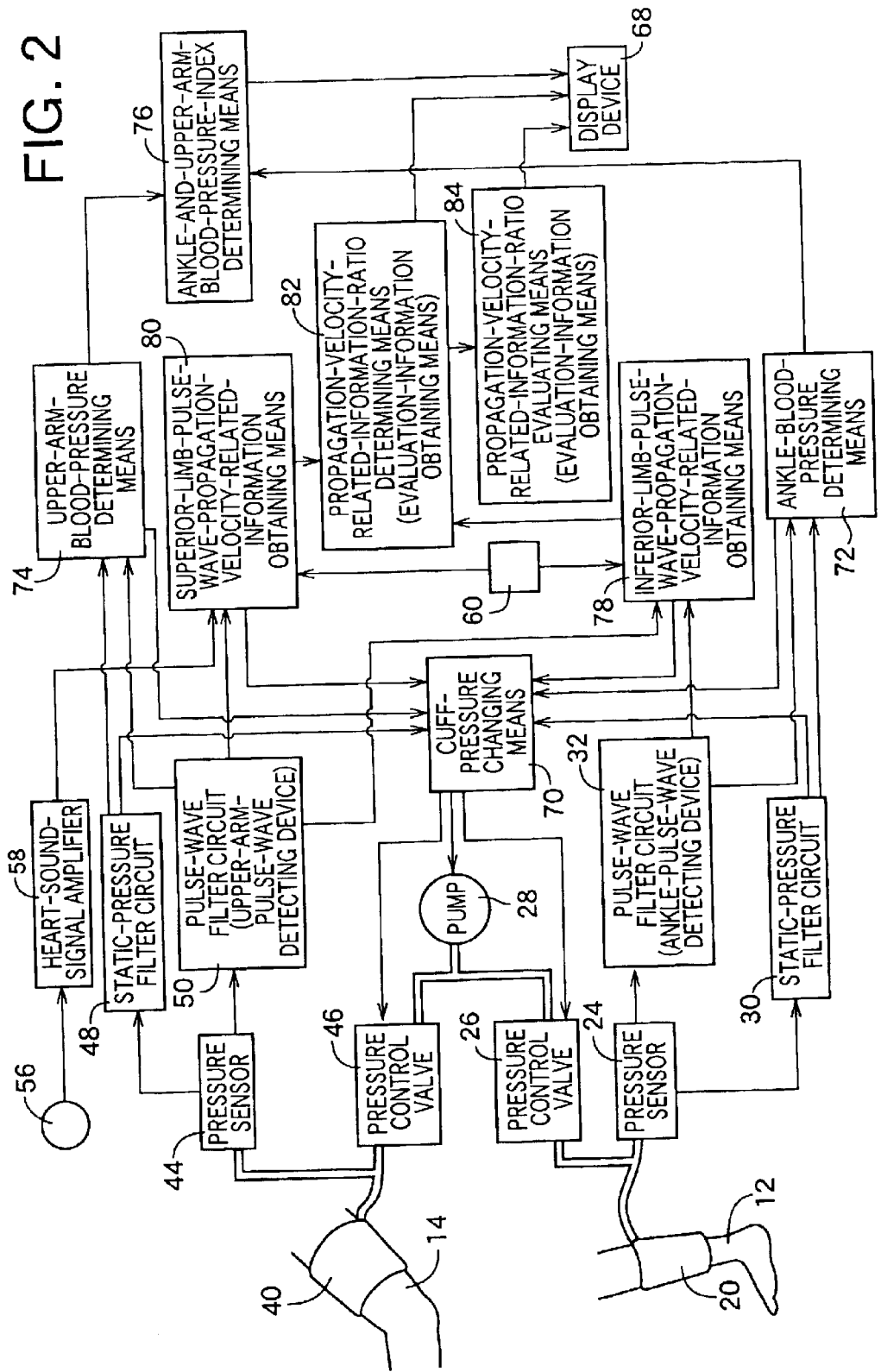
FIG. 2 is a diagrammatic view for explaining essential control functions of an electronic control device of the apparatus of FIG. 1.

FIG. 2 is a diagrammatic view for explaining essential control functions of the electronic control device 36. A cuff-pressure changing means 70 is operated according to a command signal supplied from an ankle-blood-pressure determining means 72 or an upper-arm-blood-pressure determining means 74, both described later, so as to control the air pump 28 and the two pressure control valves 26, 46 connected to the pump 28, based on the ankle-cuff-pressure signal $SC_A$ and the upper-arm-cuff-pressure signal $SC_B$ supplied from the static-pressure filter circuits 30, 48, and thereby control the ankle cuff pressure $PC_A$ and the upper-arm cuff pressure $PC_B$ as follows: First, the ankle cuff pressure $PC_A$ is quickly increased to a pre-set first target pressure $PC_{M1}$ (e.g., 240 mmHg) and the upper-arm cuff pressure SBA is quickly increased to a pre-set second target pressure (e.g., 180 mmHg). Then, the ankle cuff pressure $PC_A$ and the upper-arm cuff pressure $PC_B$ are slowly decreased at a rate of, e.g., 3 mmHg/sec. In addition, after an ankle diastolic blood pressure $BP(A)_{DIA}$ is determined, the ankle cuff pressure $PC_A$ is decreased to an atmospheric pressure; and, after an upper-arm diastolic blood pressure $BP(B)_{DIA}$ is determined, the upper-arm cuff pressure $PC_B$ is decreased to the atmospheric pressure.

In addition, the cuff-pressure changing means 70 is operated according to a command signal supplied from an inferior-limb-pulse-wave-propagation-velocity-related-information obtaining means 78 or a superior-limb-pulse-wave-propagation-velocity-related-information obtaining means 80, both described later, so as to control the air pump 28 and the two pressure control valves 26, 46 connected to the pump 28, based on the ankle-cuff-pressure signal $SC_A$ and the upper-arm-cuff-pressure signal $SC_B$ supplied from the static-pressure filter circuits 30, 48, and thereby change, and keep, the ankle cuff pressure $PC_A$ and the upper-arm cuff pressure $PC_B$ to, and at, respective pre-set pulse-wave detecting pressures.

The ankle-blood-pressure determining means 72 determines, according to a well-known oscillometric algorithm, a systolic blood pressure $BP(A)_{SYS}$, a diastolic blood pressure $BP(A)_{DIA}$, and a mean blood pressure $BP(A)_{MEAN}$ of the ankle 12, based on respective amplitudes of successive heartbeat-synchronous pulses of the ankle pulse wave continuously detected during the slow decreasing of the ankle cuff pressure $PC_A$ under the control of the pressure changing means 70. Likewise, the upper-arm-blood-pressure determining means 84 determines, according to the oscillometric algorithm, a systolic blood pressure $BP(B)_{SYS}$, a diastolic blood pressure $BP(B)_{DIA}$, and a mean blood pressure $BP(B)_{MEAN}$ of the upper arm 14, based on respective amplitudes of successive heartbeat-synchronous pulses of the upper-arm pulse wave continuously detected during the slow decreasing of the upper-arm cuff pressure $PC_B$ under the control of the pressure changing means 70.

An ankle-and-upper-arm blood-pressure-index determining means 76 determines an ABI value, based on one of the ankle blood pressure values BP(A) determined by the ankle-blood-pressure determining means 72 and a corresponding one of the upper-arm blood pressure values BP(B) determined by the upper-arm-blood-pressure determining means 74, and operates the display device 62 to display the determined ABI value. Here, for example, the ankle systolic blood pressure values BP(A) corresponds to the upper-arm systolic blood pressure values BP(B). In addition, the ABI value may be calculated by dividing the ankle blood pressure value BP(A) by the upper-arm blood pressure value BP(B), or dividing the upper-arm blood pressure value BP(B) by the ankle blood pressure value BP(A).

The inferior-limb-pulse-wave-propagation-velocity-related-information obtaining means 78 reads in the ankle-pulse-wave signal $SM_A$ supplied from the pulse-wave filter circuit 32 as an ankle-pulse-wave detecting device, and additionally reads in the upper-arm-pulse-wave signal $SM_B$ supplied from the pulse-wave filter circuit 50 as an upper-arm-pulse-wave detecting device, identifies a prescribed point (e.g., a peak point or a rising point) of the ankle pulse wave represented by the ankle-pulse-wave signal $SM_A$, and a corresponding prescribed point of the upper-arm pulse wave represented by the upper-arm-pulse-wave signal $SM_B$, and determines a time difference between a time of detection of the prescribed point of the ankle pulse wave and a time of detection of the corresponding point of the upper-arm pulse wave. Since this time difference is a pulse-wave propagation time baDT obtained from the ankle 12 and the upper arm 14, i.e., a pulse-wave propagation time obtained from a human body including an inferior limb, it can be said as an inferior-limb pulse-wave propagation time.

Moreover, the information obtaining means 78 substitutes the patient's stature T supplied from the input device 60, with the following Expression 1 that represents a relationship between stature T and propagation distance L1 and is pre-stored in the ROM 64, thereby determining a propagation distance L1 as a difference between a distance between the patient's heart and the ankle 12 and a distance between the heart and the upper arm 14, and additionally substitutes the thus determined propagation distance L1 and the above-indicated inferior-limb pulse-wave propagation time baDT, with the following Expression 2, thereby determining an inferior-limb propagation velocity baPWV (cm/sec):

$$L1=aT+b \quad \text{(Expression 1)}$$

(a and b are experimentally determined constants.)

$$baPWV=L1/baDT \quad \text{(Expression 2)}$$

The superior-limb-pulse-wave-propagation-velocity-related-information obtaining means 80 as an upper-half-body pulse-wave-propagation-velocity-related-information obtaining means, reads in the heart-sound signal SH supplied from the heart-sound microphone 56 and the upper-arm-pulse-wave signal $SM_B$ supplied from the pulse-wave filter circuit 50, substantially simultaneously when the inferior-limb-pulse-wave-propagation-velocity-related-information obtaining means 78 reads in the ankle-pulse-wave signal $SM_A$ and the upper-arm pulse wave $SM_B$, identifies a prescribed point (e.g., a starting point of a second heart sound II) of a heart-sound waveform represented by the heart-sound signal SH, and a corresponding prescribed point of the upper-arm pulse wave represented by the upper-arm-pulse-wave signal $SM_B$, and determines a time difference between a time of detection of the prescribed point of the heart-sound waveform and a time of detection of the corresponding point of the upper-arm pulse wave. Since this time difference is a pulse-wave propagation time hbDT obtained from the patient's aortic valve and the upper arm 14, i.e., a pulse-wave propagation time obtained from an upper half body including a superior limb, it can be said as a superior-limb pulse-wave propagation time or an upper-half-body pulse-wave propagation time.

Moreover, the information obtaining means 80 substitutes the patient's stature T supplied from the input device 60, with the following Expression 3 that represents a relationship between stature T and propagation distance L2 and is pre-stored in the ROM 64, thereby determining a propagation distance L2 between the aortic valve and the upper arm 14, and additionally substitutes the thus determined propagation distance L2 and the above-indicated superior-limb pulse-wave propagation time hbDT, with the following Expression 4, thereby determining a superior-limb propagation velocity hbPWV (cm/sec):

$$L2=cT+d \quad \text{(Expression 3)}$$

(c and d are experimentally determined constants.)

$$hbPWV=L2/hbDT \quad \text{(Expression 4)}$$

A propagation-velocity-related-information-ratio determining means 82 determines, as a propagation-velocity-related-information-ratio R, a ratio of one of the inferior-limb-pulse-wave-propagation-velocity-related information obtained by the inferior-limb-pulse-wave-propagation-velocity-related-information obtaining means 78 and the superior-limb-pulse-wave-propagation-velocity-related information obtained by the superior-limb-pulse-wave-propagation-velocity-related-information obtaining means 80, and operates the display device 68 to display the thus determined propagation-velocity-related-information ratio R. The propagation-velocity-related-information ratio R may be a propagation-velocity ratio R(PWV) as a value obtained by dividing the superior-limb pulse-wave propagation velocity hbPWV by the inferior-limb pulse-wave propagation velocity baPWV, or a value obtained by dividing the inferior-limb velocity baPWV by the superior-limb velocity hbPWV, or a propagation-time ratio R(DT) as a value obtained by dividing the superior-limb pulse-wave propagation time hbDT by the inferior-limb pulse-wave propagation time baDT, or a value obtained by dividing the inferior-limb time baDT by the superior-limb time hbDT. The propagation-velocity-related-information ratio R is a sort of evaluation information that is useful for evaluating reliability of the ABI value determined by the ankle-and-upper-arm blood-pressure-index determining means 76, and accordingly the propagation-velocity-related-information-ratio determining means 82 functions as a sort of evaluation-information obtaining means.

The reason why the propagation-velocity-related-information ratio R is useful for evaluating reliability of the ABI value will be described with respective to an exemplary case where the inferior-limb velocity baPWV is used as the inferior-limb-pulse-wave-propagation-velocity-related information, the superior-limb velocity hbPWV is used as the superior-limb-pulse-wave-propagation-velocity-related information, and the propagation-velocity ratio R(PWV) as the value (hbPWV/baPWV) obtained by dividing the superior-limb velocity hbPWV by the inferior-limb velocity baPWV, is used as the propagation-velocity-related-information ratio R. For example, if the patient has stenosis in an artery of the inferior limb located upstream of the ankle 12, the pulse-wave propagation velocity baPWV obtained from the inferior limb is low because of the stenosis, whereas the pulse-wave propagation velocity hbPWV obtained from the superior limb is normal. Therefore, the propagation-velocity ratio R(PWV) is higher as compared with the case where the patient does not have stenosis in the inferior limb. Thus, if the ratio R(PWV) is higher than a normal range, it is suspected that the inferior limb has stenosis. If this evaluation coincides with a judgment that is made based on the ABI value about whether the patient has stenosis in the inferior limb, it can be said that the ABI value is reliable; and, if not, it can be said that the ABI value is not reliable.

In addition, in a case where the patient has a local, advanced calcification in an artery of the inferior limb around which the ankle cuff 26 is wound, the pulse-wave propagation velocity baPWV obtained from the inferior limb is high because of the calcification, whereas the pulse-wave propagation velocity hbPWV obtained from the superior limb is normal. Therefore, the propagation-velocity ratio R(PWV) is lower as compared with the case where the patient does not have calcification in the inferior limb. In particular, if the degree of calcification of the inferior-limb artery is very high, then the propagation-velocity ratio R(PWV) is very low. In this case, the ankle cuff 26 may not be able to completely stop the flow of blood in the artery and accordingly may not be able to measure an accurate blood pressure BP(A) of the ankle 12. Thus, it can be evaluated that the reliability of the ABI value is low.

A propagation-velocity-related-information-ratio evaluating means 84 functions as a sort of evaluation-information obtaining means like the propagation-velocity-related-information-ratio obtaining means 82. The evaluating means 84 judges whether the propagation-velocity-related-information ratio R obtained by the propagation-velocity-related-information-ratio obtaining means 82 falls within a normal range which is experimentally determined in advance, and operates the display device 68 to display, as a sort of evaluation information, the result of judgment together with the ABI value and the ratio R.

Figure 3:
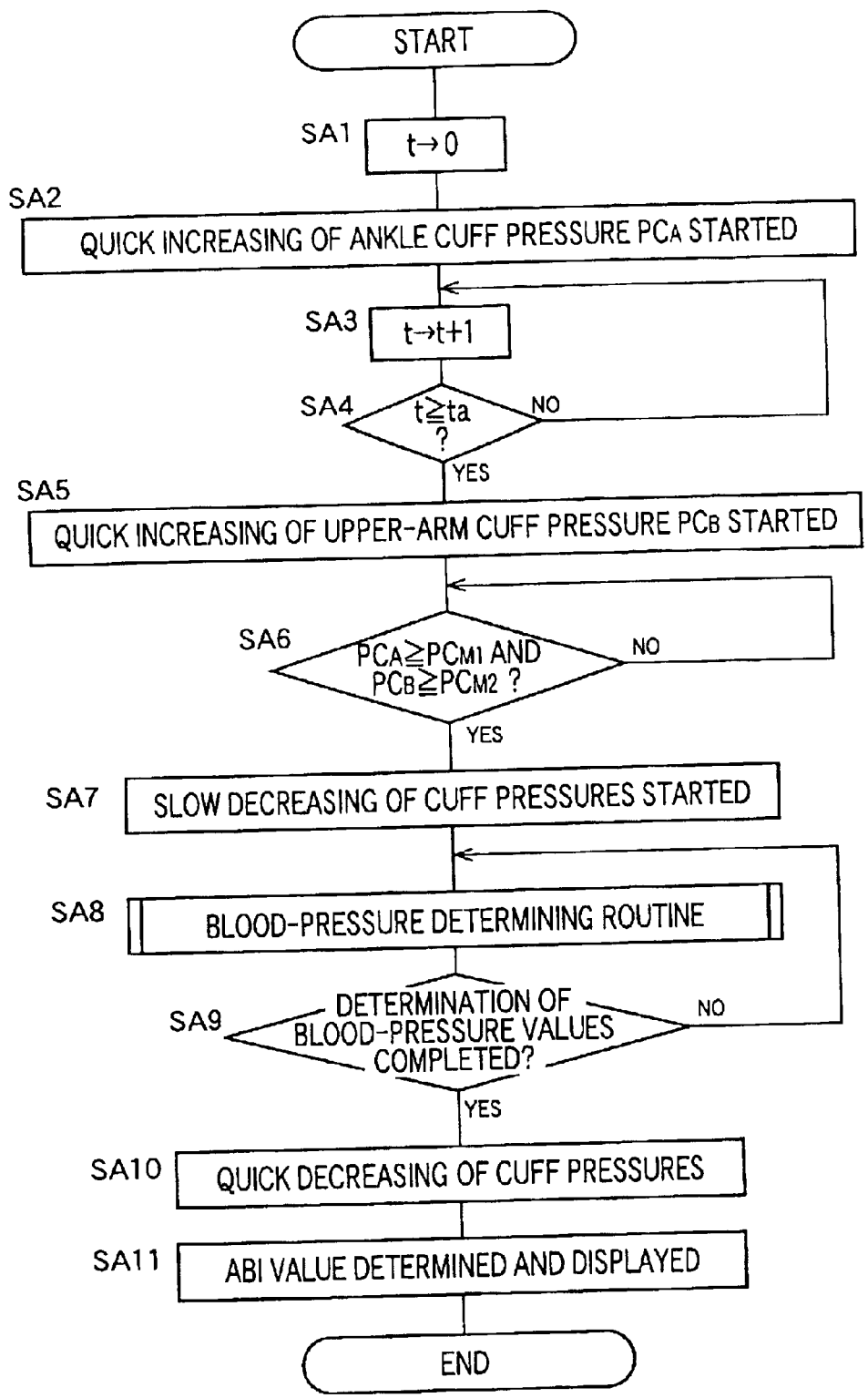
FIG. 3 is a flow chart representing some of the essential control functions of the electronic control device, shown in FIG. 2, i.e., an ABI (Ankle Arm Blood Pressure Index) determining routine.
Figure 4:
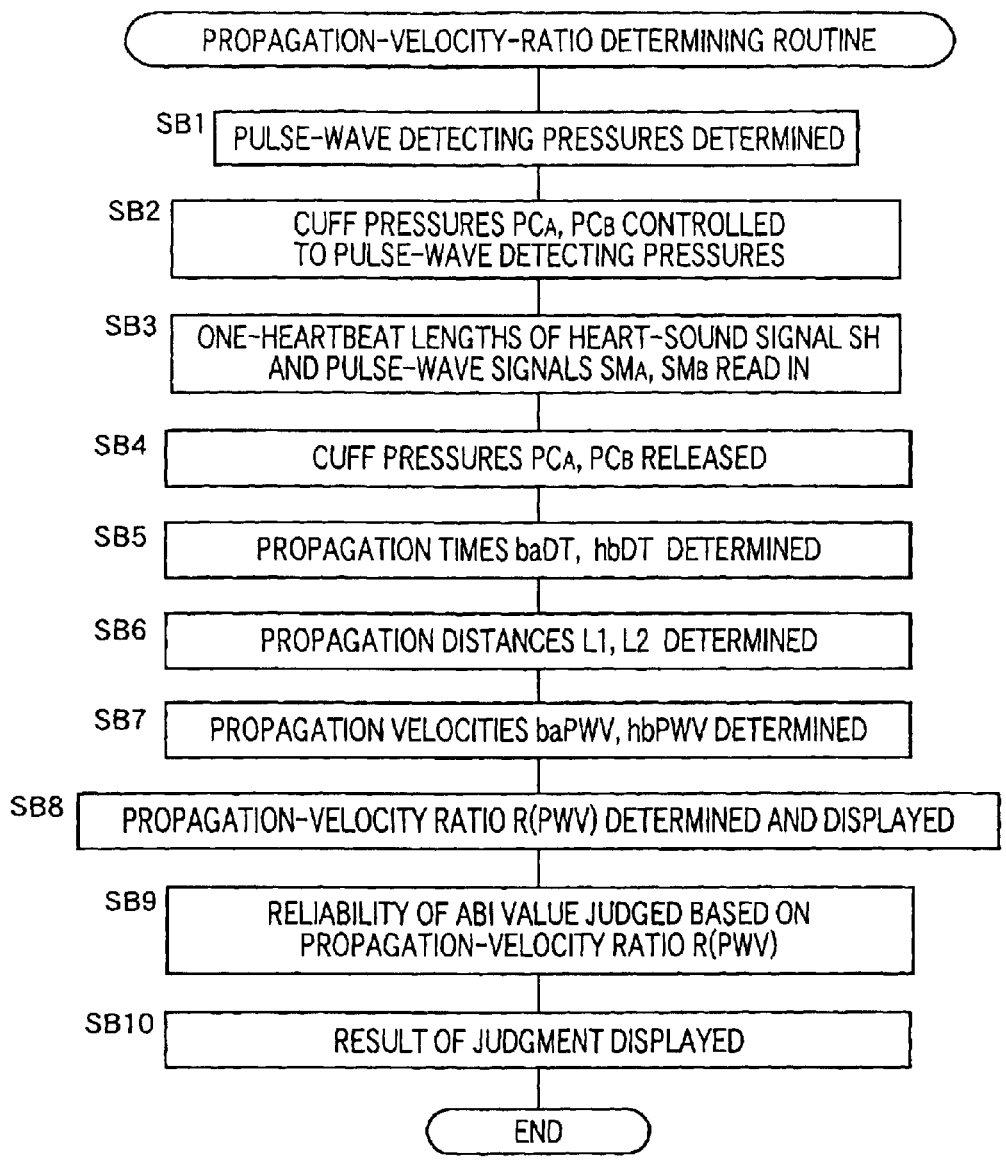
FIG. 4 is a flow chart representing some of the essential control functions of the electronic control device, shown in FIG. 2, i.e., a propagation-velocity-ratio determining routine.

FIGS. 3 and 4 are flow charts representing the essential control functions of the electronic control device 36, shown in FIG. 2. FIG. 3 shows an ABI determining routine and FIG. 4 shows a propagation-velocity-ratio determining routine following the flow chart of FIG. 3. The flow chart of FIG. 3 is started upon operation of a start button, not shown, under the condition that the control device 36 has already received, from the input device 60, the stature signal ST representing the patient's stature T.

In FIG. 3, first, at Step SA1 (hereinafter, "Step(s)" is omitted), the control device sets a timer, t, to zero. Then, at SA2, the control device drives the air pump 28 and operate the pressure control valve 26, so as to start quickly increasing the ankle cuff pressure $PC_A$. Subsequently, at SA3, the control device adds one to timer t and, at SA4, the control device judges whether a time measured by timer t has become equal to, or longer than, a delay time, ta, which is so pre-set that the ankle cuff pressure $PC_A$ and the upper-arm cuff pressure $PC_B$ may substantially simultaneously become equal to respective target pressure values $PC_{M1}$, $PC_{M2}$.

If a negative judgment is made at SA4, the control device repeats SA3 and the following steps, while measuring, with timer t, the time that has elapsed from the start of increasing of the ankle cuff pressure $PC_A$, and continuing increasing the ankle cuff pressure $PC_A$. Meanwhile, if a positive judgment is made at SA4, the control goes to SA5 to operate the pressure control valve 46 so as to start quickly increasing the upper-arm cuff pressure $PC_B$.

Then, at SA6, the control device judges whether the ankle cuff pressure $PC_A$ and the upper-arm cuff pressure $PC_B$ have become equal to, or higher than, the respective target pressure values $PC_{M1}$, $PC_{M2}$. If a negative judgment is made at SA6, the control device repeats this step. Meanwhile, if a positive judgment is made at SA6, the control goes to SA7 to stop the air pump 28 and operate the pressure control valves 26, 46 so as to slowly decrease the ankle cuff pressure $PC_A$ and the upper-arm cuff pressure $PC_B$, each at, e.g., a rate of 3 mmHg/sec.

Then, the control goes to SA8 corresponding to the ankle-blood-pressure determining means 72 and the upper-arm-pressure determining means 74, i.e., a blood-pressure determining routine. More specifically described, the control device determines respective amplitudes of successive heartbeat-synchronous pulses of the ankle pulse wave represented by the ankle-pulse-wave signal $SM_A$ continuously supplied from the pulse-wave filter circuit 32, and determines, according to a well-known oscillometric blood-pressure-determination algorithm, an ankle systolic blood pressure $BP(A)_{SYS}$, an ankle mean blood pressure $BP(A)_{MEAN}$, and an ankle diastolic blood pressure $BP(A)_{DIA}$, based on the change of the thus determined amplitudes. Similarly, the control device determines respective amplitudes of successive heartbeat-synchronous pulses of the upper-arm pulse wave represented by the upper-arm-pulse-wave signal $SM_B$ continuously supplied from the pulse-wave filter circuit 50, and determines, according to the oscillometric algorithm, an upper-arm systolic blood pressure $BP(B)_{SYS}$, an upper-arm mean blood pressure $BP(B)_{MEAN}$, and an upper-arm diastolic blood pressure $BP(B)_{DIA}$, based on the change of the thus determined amplitudes.

Then, at SA9, the control device judges whether the determination of blood-pressure values has completed. Since the diastolic blood-pressure values $BP(A)_{DIA}$, $BP(B)_{DIA}$ are last determined during the slow decreasing of the cuff pressures $PC_A$, $PC_B$, the control device judges, at SA9, whether the diastolic blood-pressure values $BP(A)_{DIA}$, $BP(B)_{DIA}$ have been determined. If a negative judgment is made at SA9, the control device repeats SA8 and the following steps. Meanwhile, if a positive judgment is made at SA9, the control goes to SA10 to operate the pressure control valves 26, 46 so as to decrease the cuff pressures $PC_A$, $PC_B$, each to an atmospheric pressure.

Subsequently, the control goes to SA11 corresponding to the ankle-and-upper-arm blood-pressure index determining means 76. At SA11, the control device divides the ankle systolic blood pressure $BP(A)_{SYS}$ determined at SA8, by the upper-arm systolic blood pressure $BP(B)_{SYS}$ also determined at SA8, thereby determining an ABI value, and operates the display device 68 to display the thus determined ABI value. SA11 is followed by the propagation-velocity-ratio determining routine shown in FIG. 4.

Next, the propagation-velocity-ratio determining routine shown in FIG. 4 will be described. First, at SB1, the control device subtracts a pre-set pressure value, a, e.g., 10 mmHg, from the ankle diastolic blood pressure $BP(A)_{DIA}$ determined at SA8 of FIG. 3, thereby determining a pulse-wave detecting pressure with respect to the ankle 12. Similarly, the control device subtracts the pre-set pressure value α from the upper-arm diastolic blood pressure $BP(B)_{DIA}$ also determined at SA8 of FIG. 3, thereby determining a pulse-wave detecting pressure with respect to the upper arm 14. Then, at SB2, the control device again drives the air pump 28 and operates the pressure control valves 26, 46 so as to change and keep the ankle cuff pressure $PC_A$ and the upper-arm cuff pressure $PC_B$ to the respective pulse-wave detecting pressures determined at SB1.

Then, at SB3, the control device reads in respective one-heartbeat lengths of the heart-sound signal SH supplied from the heart-sound microphone 56 via the amplifier 58, the ankle-pulse-wave signal $SM_A$ supplied from the pulse-wave filter circuit 32, and the upper-arm-pulse-wave signal $SM_B$ supplied from the pulse-wave filter circuit 50. Thereafter, the control goes to SB4 to stop the air pump 28 and operate the pressure control valves 26, 46 so as to release the ankle cuff pressure $PC_A$ and the upper-arm cuff pressure $PC_B$, each to an atmospheric pressure. In the flow charts shown in FIGS. 3 and 4, SA1 to SA7, SA10, SB1, SB2, and SB4 correspond to the cuff-pressure changing means 70.

Then, the control goes to SB5 to SB7 corresponding to the inferior-limb-pulse-wave propagation-velocity-related-information obtaining means 78 and the superior-limb-pulse-wave propagation-velocity-related-information obtaining means 80. First, at SB5, the control device identifies a starting point of a second heart sound II on the waveform of the heart-sound signal, a rising point of the waveform of the ankle-pulse-wave signal, a rising point of the waveform of the upper-arm-pulse-wave signal and a dichroitic notch of waveform of the upper-arm-pulse-wave signal also those signals having been read in at SB3. Then, the control device determines, as an inferior-limb pulse-wave propagation time baDT, a time difference between a time of occurrence of the rising point of the upper-arm pulse wave and a time of occurrence of the rising point of the ankle pulse wave, and determines, as a superior-limb pulse-wave propagation time hbDT, a time difference between a time of occurrence of the starting point of the second heart sound II and a time of occurrence of the notch of the upper-arm pulse wave that corresponds to the starting point of the second heart sound II.

Then, at SB6, the control device substitutes the patient's stature T that has been supplied thereto in advance, with each of the above-indicated Expression 1 and Expression 3, thereby determining respective propagation distances L1, L2. SB6 is followed by SB7 to substitute the inferior-limb pulse-wave propagation time baDT determined at SB5 and the propagation distance L1 determined at SB6, with the above-indicated Expression 2, thereby determining, an inferior-limb pulse-wave propagation velocity baPWV, and substitute the superior-limb pulse-wave propagation time hbDT determined at SB5 and the propagation distance L2 determined at SB6, with the above-indicated Expression 4, thereby determining a superior-limb pulse-wave propagation velocity hbPWV.

Then, the control goes to SB8 corresponding to the propagation-velocity-related-information-ratio determining means 82. At SB8, the control device divides the superior-pulse-wave propagation velocity hbPWV determined at S7, by the inferior-pulse-wave propagation velocity baPWV also determined at S7, thereby determining a propagation-velocity ratio R(PWV), and operates the display device 68 to display the thus determined propagation-velocity ratio R(PWV).

Next, the control goes to SB9 and SB10 corresponding to the propagation-velocity-related-information-ratio evaluating means 84. First, at SB9, the control device judges whether the propagation-velocity ratio R(PWV) determined at SB8 falls within a pre-set normal range. If a positive judgment is made, then the control device judges that the ABI value determined at SA11 of FIG. 3 is reliable; and if the ratio R(PWV) is smaller than a lower limit (e.g., 0.35) of the normal range, the control device judges that the ABI value is not reliable. If the propagation-velocity ratio R(PWV) is greater than an upper limit of the normal range, the control device additionally judges whether the ABI value is lower than a lower limit of a pre-set normal range and accordingly is abnormal. If the ABI value is abnormal, the control device judges that the ABI is reliable; and if the ABI value is normal, then the control device judges that the ABI value is not reliable.

Subsequently, at SB10, the control device operates the display device 68 to display the result of judgment made at SB9, i.e., display characters representing evaluation about whether the ABI value being displayed is reliable.

In the embodiment employing the flow charts shown in FIGS. 3 and 4, at SB8 (the propagation-velocity-related-information-ratio determining means 82), the control device determines the propagation-velocity ratio R(PWV) as the ratio of the superior-limb pulse-wave propagation velocity hbPWV to the inferior-limb pulse-wave propagation velocity baPWV, each determined at SB7 (the inferior-limb-pulse-wave-propagation-velocity-related-information obtaining means 78 and the superior-limb-pulse-wave-propagation-velocity-related-information obtaining means 80), and operates the display device 68 to display the thus determined propagation-velocity ratio R(PWV). Here, it is noted that the inferior-limb pulse-wave propagation velocity baPWV is a pulse-wave propagation velocity PWV measured with respect to a region including the ankle 12 and the upper arm 14 and accordingly indicates arteriosclerosis of the region including the ankle 12 and the upper arm 14, and that the superior-limb pulse-wave propagation velocity hbPWV is a pulse-wave propagation velocity PWV measured with respect to a region including the patient's aortic valve and the upper arm 14 and accordingly indicates arteriosclerosis of the region including the aortic valve and the upper arm 14. Therefore, if the patient has stenosis in the artery of the inferior limb, the inferior-limb pulse-wave propagation velocity baPWV is influenced by the stenosis, whereas the superior-limb pulse-wave propagation velocity hbPWV is not influenced. That is, the propagation-velocity ratio R(PWV) changes with the stenosis. This is the reason why the reliability of the ABI value can be evaluated based on the propagation-velocity ratio R(PWV). In addition, the propagation-velocity ratio R(PWV) is a ratio derived from the inferior-limb pulse-wave propagation velocity baPWV and the superior-limb pulse-wave propagation velocity hbPWV, both actually obtained from each individual patient, the ratio R(PWV) is not influenced by differences of individual patients and/or physical conditions of each individual patient. Thus, the reliability of the ABI value can be evaluated with accuracy based on the ratio R(PWV).

In the embodiment employing the flow charts shown in FIGS. 3 and 4, at S9 and S10 (the propagation-velocity-ratio evaluating means 84), the control device judges whether the propagation-velocity ratio R(PWV) falls within the pre-set normal range, thereby judging whether the reliability of the ABI value determined at SA11 (the ankle-and-upper-arm blood-pressure-index determining means 76) is high, and operates the display device 68 to display the result of judgment made. Thus, the reliability of the ABI value can be easily recognized by a medical person such as a doctor or a nurse.

Next, there will be described another embodiment of the present invention. In the following description, the same reference numerals as used in the above-described embodiment are used to designate the corresponding elements and the description thereof is omitted.

Figure 5:
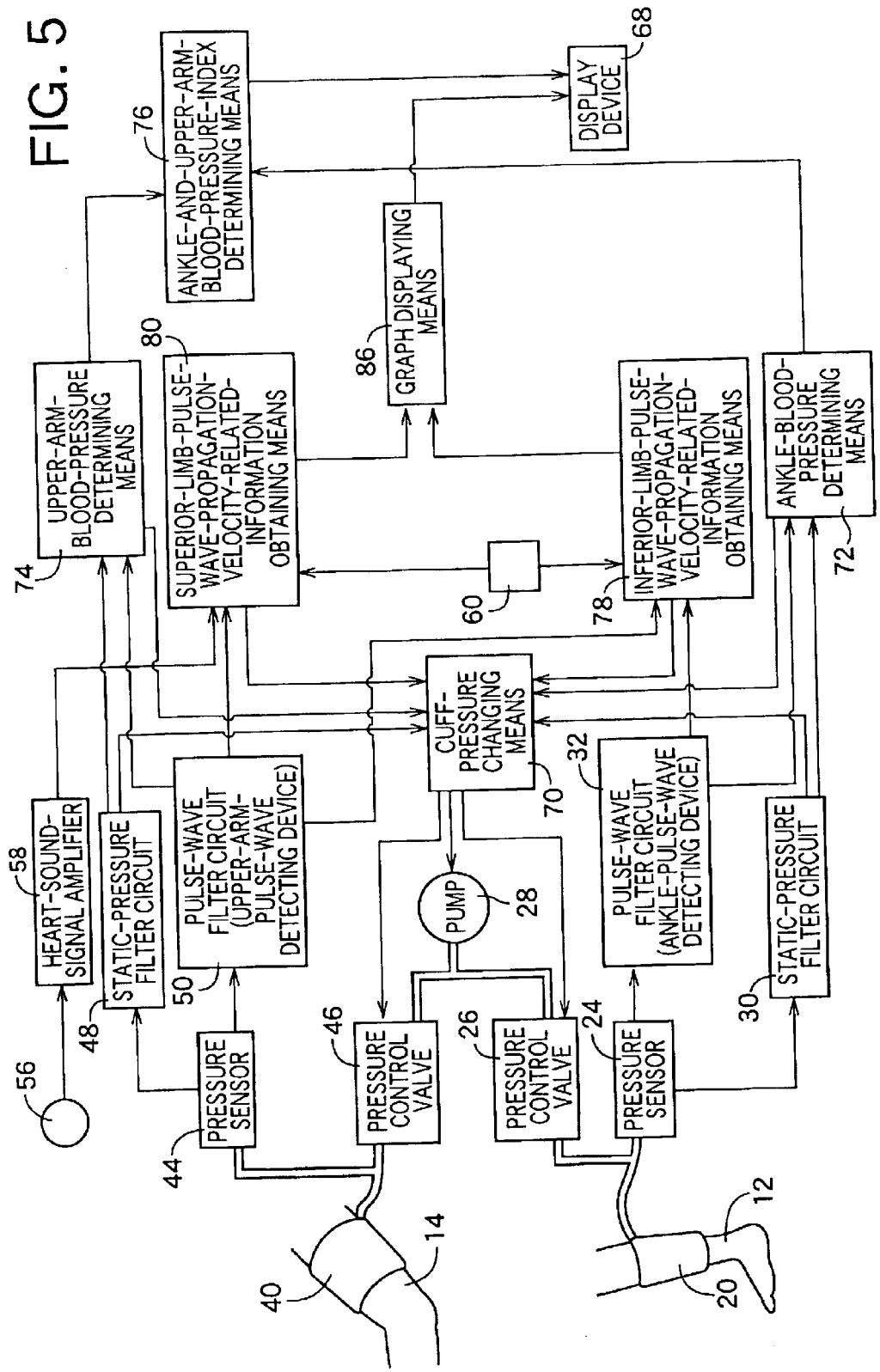
FIG. 5 is a diagrammatic view for explaining essential control functions of an electronic control device of another ankle-and-upper-arm blood-pressure-index measuring apparatus different from the apparatus of FIG. 1.

FIG. 5 is a diagrammatic view showing essential control functions of an electronic control device 36 of another ankle-and-upper-arm blood-pressure index measuring device different from the ankle-and-upper-arm blood-pressure index measuring device 10 shown in FIG. 1. The present apparatus differs from the apparatus of FIG. 10, with respect to only some of the control functions of the control device 36.

The control functions of the control device 36 shown in FIG. 5 differs from those of the control device 36 shown in FIG. 2, only in that the former control functions do not include the propagation-velocity-related-information-rate determining means 82 or the propagation-velocity-related-information-rate evaluating means 84, and additionally employs a graph displaying means 86.

The graph displaying means 86 operates the display device 68 to display a two-dimensional coordinate system which is defined by a first axis indicative of inferior-limb-pulse-wave-propagation-velocity-related information and a second axis indicative of superior-limb-pulse-wave-propagation-velocity-related information, and which includes indication of a normal range of superior-limb-pulse-wave-propagation-velocity-related information relative to inferior-limb-pulse-wave-propagation-velocity-related information, and to display, in the two-dimensional coordinate system, a symbol at a position corresponding to the inferior-limb-pulse-wave-propagation-velocity-related information obtained by the inferior-limb-pulse-wave-propagation-velocity-related-information obtaining means 78 and the upper-half-body-pulse-wave-propagation-velocity-related information obtained by the upper-half-body-pulse-wave-propagation-velocity-related-information obtaining means 80.

Figure 6:
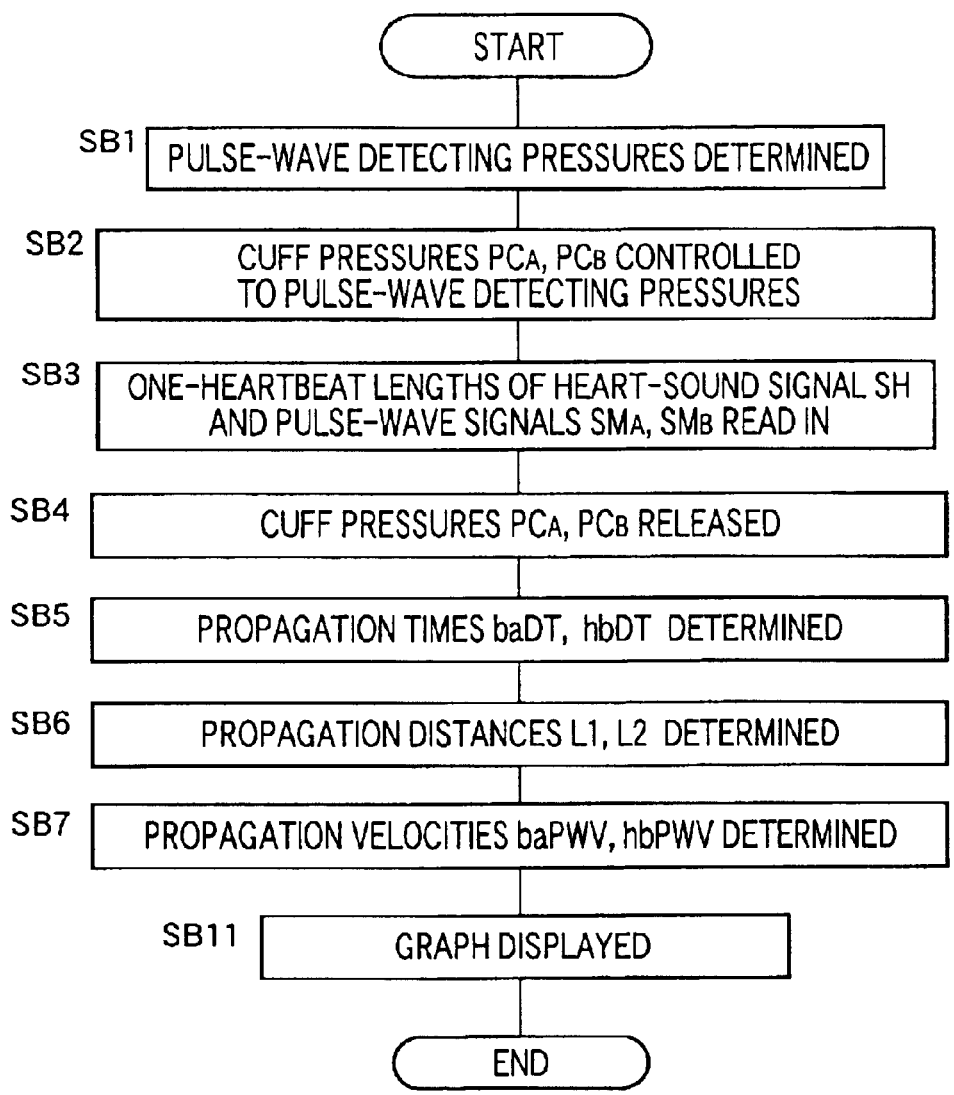
FIG. 6 is a flow chart corresponding to FIG. 4, representing some of essential control functions of the electronic control device, shown in FIG. 5.

FIG. 6 is a flow chart representing the control functions of the control device 36 shown in FIG. 5, and corresponding to the flow chart shown in FIG. 4. The flow chart of FIG. 6 follows, like the flow chart of FIG. 4, the flow chart of FIG. 3.

Figure 7:
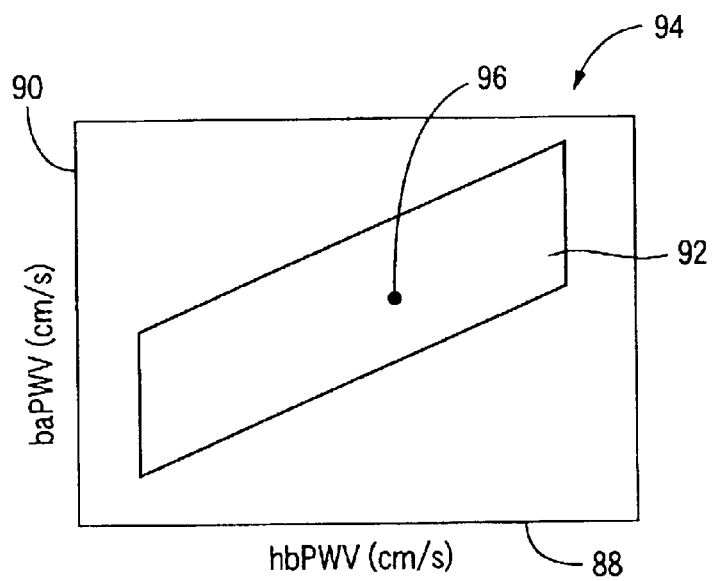
FIG. 7 is a view showing an example of a two-dimensional graph which is displayed by a display device at Step SB11 shown in FIG. 6.

The flow chart of FIG. 6 differs from the flow chart of FIG. 4 only in that the former flow chart employs SB11 in place of SB8 to SB10 of the latter flow chart. At SB11, the control device display, as shown in FIG. 7, a two-dimensional coordinate system 94 which is defined by an axis 88 indicative of inferior-limb-pulse-wave propagation velocity and an axis 90 indicative of superior-limb-pulse-wave propagation velocity, and which includes indication of a normal range or area 92 of superior-limb pulse-wave propagation velocity hbPWV relative to inferior-limb-pulse-wave propagation velocity baPWV, and to display, in the two-dimensional coordinate system 88, a symbol 96 at a position corresponding to the inferior-limb-pulse-wave propagation velocity baPWV determined at SB7 and the superior-limb-pulse-wave propagation velocity hbPWV also determined at SB7.

If the symbol 96 does not fall within the normal area 92 displayed in the two-dimensional coordinate system 94 by the display device 68, the patient is suspected to have stenosis in the artery of the inferior limb. More specifically described, if the patient has stenosis in the artery of the inferior limb located upstream of the ankle 12, the inferior-limb pulse-wave propagation velocity baPWV is lower than a normal velocity because of the influence of the stenosis, whereas the superior-limb pulse-wave propagation velocity hbPWV is normal with no influence of the stenosis. Therefore, the symbol 96 does not fall in the normal area 92. If this result coincides with the judgment made based on the ABI value about whether the inferior limb has stenosis, then the ABI value is reliable; and, if not, the measurement of the ABI value is suspected to have been not normal.

In the present embodiment, the control device operates the display device 68 to display, in the two-dimensional coordinate system 94 including the indication of the normal range 92 of the superior-limb pulse-wave propagation velocity hbPWV relative to the inferior-limb pulse-wave propagation velocity baPWV, the graphical representation or symbol 96 at the position corresponding to the inferior-limb pulse-wave propagation velocity baPWV and the superior-limb pulse-wave propagation velocity hbPWV, both determined at SB7 (the inferior-limb-pulse-wave-propagation-velocity-related-information obtaining means 78 and the superior-limb-pulse-wave-propagation-velocity-related-information obtaining means 80). Thus, a person can easily judge whether the relationship between the inferior-limb pulse-wave propagation velocity baPWV and the superior-limb pulse-wave propagation velocity hbPWV, is normal, and accordingly can easily evaluate the reliability of the ABI value.

While the present invention has been described in its embodiments by reference to the drawings, it is to be understood that the invention may otherwise be embodied.

For example, in each of the illustrated embodiments, the upper-half-body-pulse-wave-propagation-velocity-related information is obtained in the form of the superior-limb pulse-wave propagation velocity hbPWV with respect to the portion between the artic valve and the upper arm 14, i.e., a pulse-wave propagation velocity with respect to a portion including a superior limb. However, the upper-half-body-pulse-wave-propagation-velocity-related information may be obtained in the form of pulse-wave-propagation-velocity-related information with respect to a portion not including a superior limb, e.g., a portion between the heart and the neck.

In addition, in each of the illustrated embodiments, the inferior-limb-pulse-wave-propagation-velocity-related-information obtaining means 78 obtains, as the inferior-limb-pulse-wave-propagation-velocity-related information, the pulse-wave-propagation-velocity-related information with respect to the portion including the ankle 12 and the upper arm 14. However, each of the first embodiment shown in FIGS. 1 to 4 and the second embodiment shown in FIGS. 5 to 7 may be modified to additionally employ a pulse-wave detecting device which has a construction identical with that of the ankle-blood-pressure measuring device 16 and which detects, like the pulse-wave filter circuit 32, a femoral pulse wave from a femoral portion of the patient. In this case, the inferior-limb-pulse-wave-propagation-velocity-related information may be obtained in the form of pulse-wave-propagation-velocity-related information with respect to a portion between the femoral portion and the ankle 12. Moreover, it may not be needed, unlike the illustrated embodiments, to obtain, as the upper-half-body-pulse-wave-propagation-velocity-related information, the pulse-wave propagation velocity with respect to the portion between the artic valve and the upper arm 14. That is, the upper-half-body-pulse-wave-propagation-velocity-related information may be obtained in the form of pulse-wave propagation velocity with respect to, e.g., a portion including an inferior limb, so long as the portion includes at least a portion of an upper half body of the patient. For example, the upper-half-body-pulse-wave-propagation-velocity-related information may be obtained in the form of pulse-wave propagation velocity with respect to a portion including the upper arm 14 and the ankle 12.

In each of the above-indicated modified first and second embodiments in which the inferior-limb-pulse-wave-propagation-velocity-related information is obtained in the form of the pulse-wave-propagation-velocity-related information with respect to the portion between the femoral portion and the ankle 12, and the upper-half-body-pulse-wave-propagation-velocity-related information is obtained in the form of the pulse-wave propagation velocity with respect to the portion including the upper arm 14 and the ankle 12, the inferior-limb-pulse-wave-propagation-velocity-related information indicates arteriosclerosis of the portion between the femoral portion and the ankle 12, and the upper-half-body-pulse-wave-propagation-velocity-related information indicates arteriosclerosis of the portion including the upper arm 14 and the ankle 12. Therefore, if the patient has stenosis in the artery of the inferior limb, the inferior-limb-pulse-wave-propagation-velocity-related information is strongly influenced by the stenosis, whereas the upper-half-body-pulse-wave-velocity-related information is not influenced so strongly. Thus, in the modified first embodiment, a propagation velocity ratio R(PWV) is determined and utilized in the same manners as those employed in the first embodiment; and in the modified second embodiment, inferior-limb-pulse-wave-propagation-velocity-related information and upper-half-body-pulse-wave-propagation-velocity-related information are graphically displayed in a two-dimensional coordinate system including respective indications of respective normal ranges of the two sorts of information, in the same manner as that employed in the second embodiment.

Inferior-limb-pulse-wave-propagation-velocity-related information and upper-half-body-pulse-wave-propagation-velocity-related information may be obtained from respective different portions of the patient than the above-described portions. For example, inferior-limb-pulse-wave-propagation-velocity-related information may be obtained in the form of pulse-wave-propagation-velocity-related information with respect to a portion between the heart and the ankle 12; and upper-half-body-pulse-wave-propagation-velocity-related information may be obtained in the form of pulse-wave-propagation-velocity-related information with respect to a portion between the heart and the upper arm 14 of the patient.

In the first embodiment, the propagation-velocity ratio is determined as the comparison between the inferior-limb-pulse-wave-propagation-velocity-related information and the superior-limb-pulse-wave-propagation-velocity-related information. However, a difference between the two sorts of information may be obtained as the comparison.

In each of the illustrated embodiments, the heart-sound microphone 56 may be replaced with a device for detecting an electrocardiogram, i.e., an electrocardiograph that includes a plurality of electrodes adapted to be worn on respective prescribed locations of a living subject and detects an electrocardiographic signal through the electrodes. In this case, the electrocardiographic signal is used to obtain pulse-wave-propagation-velocity-related information. In addition, each of the cuffs 20, 40 may be replaced with a pressure-pulse-wave sensor, a photoelectric-pulse-wave sensor, or an impedance-pulse-wave sensor, and a pulse wave detected by the sensor my be used to obtain pulse-wave-propagation-velocity-related information.

In the first embodiment, the display device 68 displays, as the evaluation information, the propagation-velocity-related-information ratio R and the result of judgment made based on the ratio R. However, the display device 68 may be modified to display only one of the ratio R or the result of judgment. In addition, at SB10 of FIG. 4, the result of judgment is displayed in the form of characters, together with the ABI value, on the display device 68. However, the result of judgment may be indicated by lighting of a light-emitting element such as an LED (light emitting diode).

It is to be understood that the present invention may be embodied with other changes, improvements and modifications that may occur to a person skilled in the art without departing from the spirit and scope of the invention defined in the appended claims.

What is claimed is:

1. An apparatus for measuring an inferior-and-superior-limb blood-pressure index of a living subject, comprising:

an inferior-limb blood-pressure measuring device which includes an inferior-limb cuff adapted to be wound around an inferior limb of the subject and measures a blood pressure of the inferior limb;

a superior-limb blood-pressure measuring device which includes a superior-limb cuff adapted to be wound around a superior limb of the subject and measures a blood pressure of the superior limb;

an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device;

an inferior-limb-pulse-wave-propagation-velocity-related-information obtaining device which obtains inferior-limb-pulse-wave-propagation-velocity-related information that is related to a velocity at which an inferior-limb pulse wave propagates in a first portion of the subject that includes the inferior limb;

an upper-half-body-pulse-wave-propagation-velocity-related-information obtaining device which obtains upper-half-body-pulse-wave-propagation-velocity-related information that is related to a velocity at which an upper-half-body pulse wave propagates in a second portion of an upper half body of the subject; and an evaluation-information obtaining means for obtaining, based on comparison of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device, evaluation information that is related to evaluation of reliability of the inferior-and-superior-limb blood-pressure index determined by the inferior-and-superior-limb-blood-pressure-index determining means.

2. An apparatus according to claim 1, wherein the inferior-limb blood-pressure measuring device includes the inferior-limb cuff adapted to be wound around an ankle of the subject and measures a blood pressure of the ankle, wherein the superior-limb blood-pressure measuring device includes the superior-limb cuff adapted to be wound around an upper arm of the subject and measures a blood pressure of the upper arm, wherein the inferior-limb-pulse-wave-propagation-velocity-related-information obtaining device obtains the inferior-limb-pulse-wave-propagation-velocity-related information related to the velocity at which the inferior-limb pulse wave propagates in the first portion of the subject that includes the ankle and the upper arm, and wherein the upper-half-body-pulse-wave-propagation-velocity-related-information obtaining device obtains the upper-half-body-pulse-wave-propagation-velocity-related information related to the velocity at which the upper-half-body pulse wave propagates in the second portion of the upper half body of the subject that includes a portion between the heart of the subject and the upper arm of the subject.

3. An apparatus according to claim 1, wherein the evaluation-information obtaining means obtains, as the evaluation information, a ratio of one of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device to the other of the inferior-limb-pulse-wave-propagation-velocity-related information and the upper-half-body-pulse-wave-propagation-velocity-related information.

4. An apparatus according to claim 3, wherein the evaluation-information obtaining means judges whether the ratio of said one of the inferior-limb-pulse-wave-propagation-velocity-related information and the upper-half-body-pulse-wave-propagation-velocity-related information to the other of the inferior-limb-pulse-wave-propagation-velocity-related information and the upper-half-body-pulse-wave-propagation-velocity-related information falls within a pre-set normal range, and thereby automatically judges whether the inferior-and-superior-limb blood-pressure index is reliable.

5. An apparatus according to claim 1, wherein the evaluation-information obtaining means obtains, as the evaluation information, a difference of one of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upper-half-body-pulse-wave-propagation-velocity-related-information obtaining device from the other of the inferior-limb-pulse-wave-propagation-velocity-related information and the upper-half-body-pulse-wave-propagation-velocity-related information.

6. An apparatus according to claim 5, wherein the evaluation-information obtaining means judges whether the difference of said one of the inferior-limb-pulse-wave-propagation-velocity-related information and the upper-half-body-pulse-wave-propagation-velocity-related information from the other of the inferior-limb-pulse-wave-propagation-velocity-related information and the upper-half-body-pulse-wave-propagation-velocity-related information falls within a pre-set normal range, and thereby automatically judges whether the inferior-and-superior-limb blood-pressure index is reliable.

7. An apparatus for measuring an inferior-and-superior-limb blood-pressure index of a living subject, comprising:

an inferior-limb blood-pressure measuring device which includes an inferior-limb cuff adapted to be wound around an inferior limb of the subject and measures a blood pressure of the inferior limb;

a superior-limb blood-pressure measuring device which includes a superior-limb cuff adapted to be wound around a superior limb of the subject and measures a blood pressure of the superior limb;

an inferior-and-superior-limb-blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device;

an inferior-limb-pulse-wave-propagation-velocity-related-information obtaining device which obtains inferior-limb-pulse-wave-propagation-velocity-related information that is related to a velocity at which an inferior-limb pulse wave propagates in a first portion of the inferior limb of the subject;

an upper-half-body-pulse-wave-propagation-velocity-related-information obtaining device which obtains upper-half-body-pulse-wave-propagation-velocity-related information that is related to a velocity at which an upper-half-body pulse wave propagates in a second portion of the subject that includes an upper half body of the subject; and an evaluation-information obtaining means for obtaining, based on comparison of the inferior-limb-pulse-wave-propagation-velocity-related information obtained by the inferior-limb-pulse-wave-propagation-velocity-related-information obtaining device and the upper-half-body-pulse-wave-propagation-velocity-related information obtained by the upperhalf-body-pulse-wave-propagation-velocity-related-information obtaining device, evaluation information that is related to evaluation of reliability of the inferior-and-superior-limb blood-pressure index determined by the inferior-and-superior-limb-blood-pressure-index determining means.

* * * * *